US006994086B1

(12) United States Patent
Martinez et al.

(10) Patent No.: US 6,994,086 B1
(45) Date of Patent: Feb. 7, 2006

(54) STANDBY REGULATOR FOR BREATHING SYSTEM

(75) Inventors: Patrice Martinez, Le Perray en Yvelines (FR); Michel Bardel, Maurepas (FR)

(73) Assignee: Intertechnique, Plaisir (FR)

( * ) Notice: Subject to any disclaimer, the term of this patent is extended or adjusted under 35 U.S.C. 154(b) by 0 days.

(21) Appl. No.: 09/744,303

(22) PCT Filed: Jul. 22, 1999

(86) PCT No.: PCT/FR99/01803

§ 371 (c)(1),
(2), (4) Date: Jan. 23, 2001

(87) PCT Pub. No.: WO00/04956

PCT Pub. Date: Feb. 3, 2000

(30) Foreign Application Priority Data

Jul. 24, 1998 (FR) .................................. 98 09493

(51) Int. Cl.
*A61M 16/00* (2006.01)

(52) U.S. Cl. .......................... 128/204.26; 128/205.24; 128/205.11; 137/908

(58) Field of Classification Search .......... 128/204.26, 128/204.21, 204.23, 204.28, 206.27, 205.24, 128/207.11, 206.21, 205.11; 137/908
See application file for complete search history.

(56) References Cited

U.S. PATENT DOCUMENTS 3,073,301 A * 1/1963 Hay et al. ............. 128/205.24
3,077,881 A * 2/1963 Sprague ................. 128/204.28
3,599,636 A * 8/1971 Gutman et al. ........ 128/207.11
3,768,466 A * 10/1973 Johnson ................. 128/204.26
4,127,129 A * 11/1978 Cramer .................. 128/204.28
4,240,419 A * 12/1980 Furlong et al. ........ 128/204.23
4,335,735 A * 6/1982 Cramer et al. ............. 137/81.1
4,336,590 A * 6/1982 Jacq et al. ............. 128/204.21
4,437,462 A * 3/1984 Piljay et al. ........... 128/207.11
4,572,176 A * 2/1986 Walther ................. 128/204.26
4,664,108 A * 5/1987 Ansite ................... 128/202.26
4,915,106 A * 4/1990 Aulgur et al. ......... 128/207.11
5,036,846 A * 8/1991 Aulgur et al. ......... 128/207.11
5,488,948 A * 2/1996 Dubruille et al. ...... 128/207.11
5,499,624 A * 3/1996 Kruger et al. ......... 128/204.26
5,503,147 A * 4/1996 Bertheau ............... 128/207.11
5,623,923 A * 4/1997 Bertheau et al. ....... 128/207.11
5,690,102 A * 11/1997 Bertheau et al. ....... 128/207.11
5,771,886 A * 6/1998 Maire et al. ........... 128/207.11
5,941,245 A * 8/1999 Hannah et al. ........ 128/207.11
5,954,052 A * 9/1999 McDonald et al. .... 128/206.27
6,039,045 A * 3/2000 Bertheau et al. ....... 128/207.11
6,470,887 B1 * 10/2002 Martinez ............... 128/207.11

* cited by examiner

*Primary Examiner*—Mital Patel
(74) *Attorney, Agent, or Firm*—Stites & Harbison PLLC; Douglas E. Jackson

(57) ABSTRACT

The demand regulator has a duct communicating a pressurized breathing gas admission with a tube connected to the inside of a breathing mask. Dilution air may be added to the breathing gas. A breathe-out valve opens from the tube to atmosphere. A manual control member has a normal position causing operation without an over pressure above atmosphere and with dilution and an emergency position causing the tube to be fed with pure breathing gas (typically oxygen) at high pressure. Operation with over pressure gas feed is prevented mechanically or pneumatically so long as the mask is being stored.

5 Claims, 3 Drawing Sheets

FIG.1.
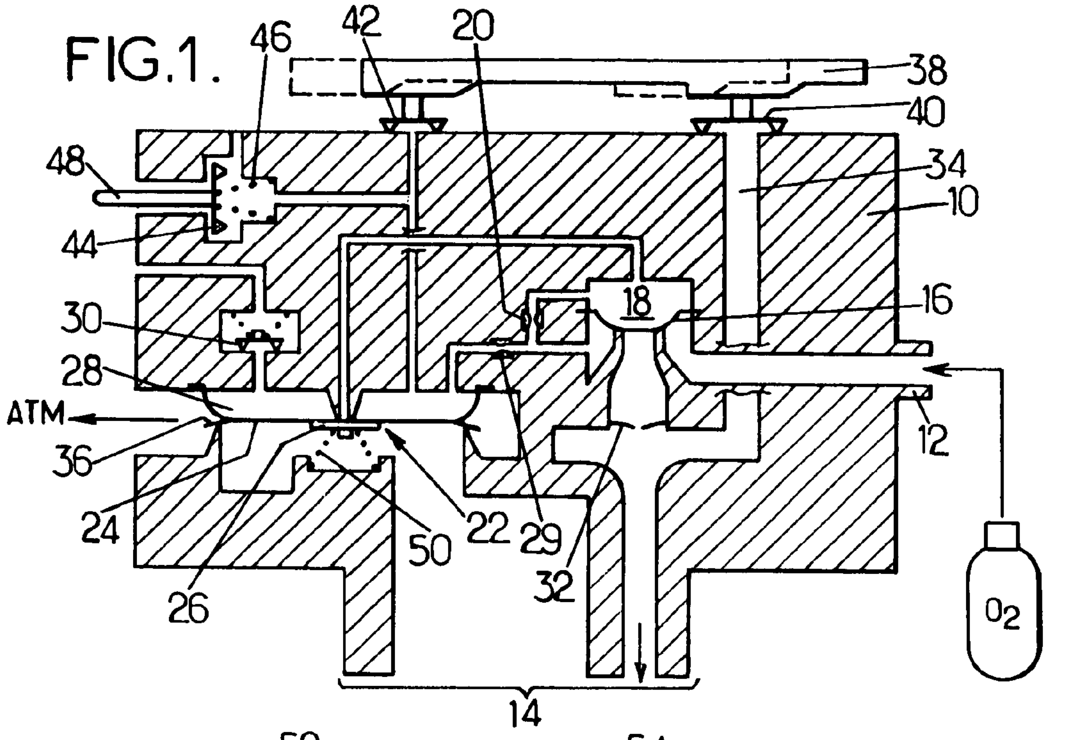
FIG.2
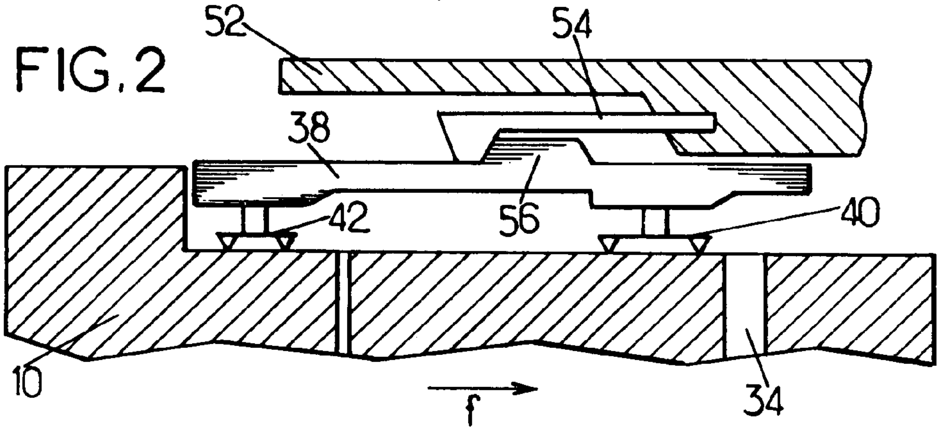
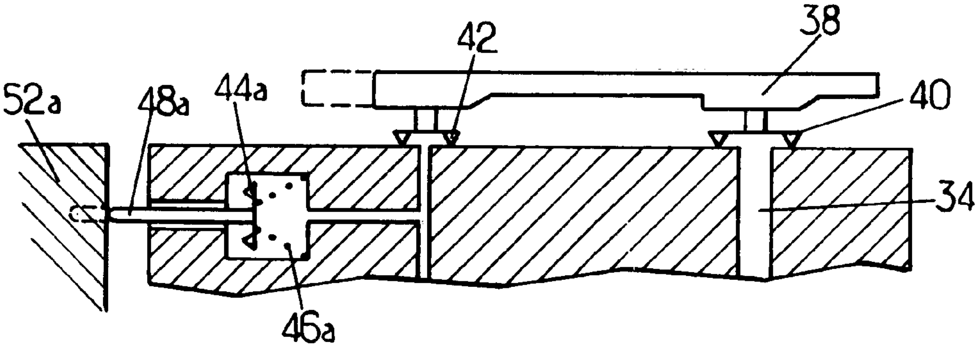
FIG.3.

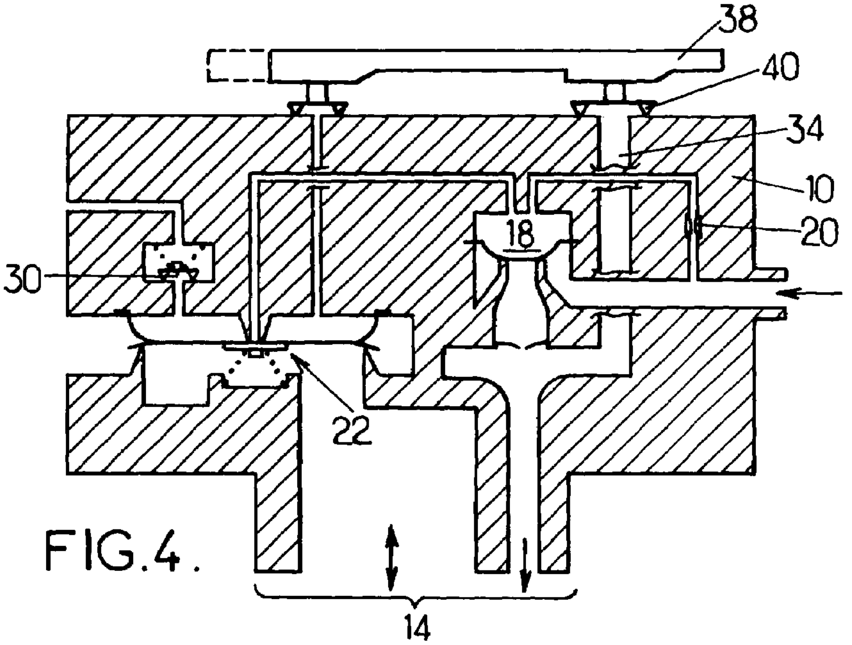
FIG.4.
FIG.6.
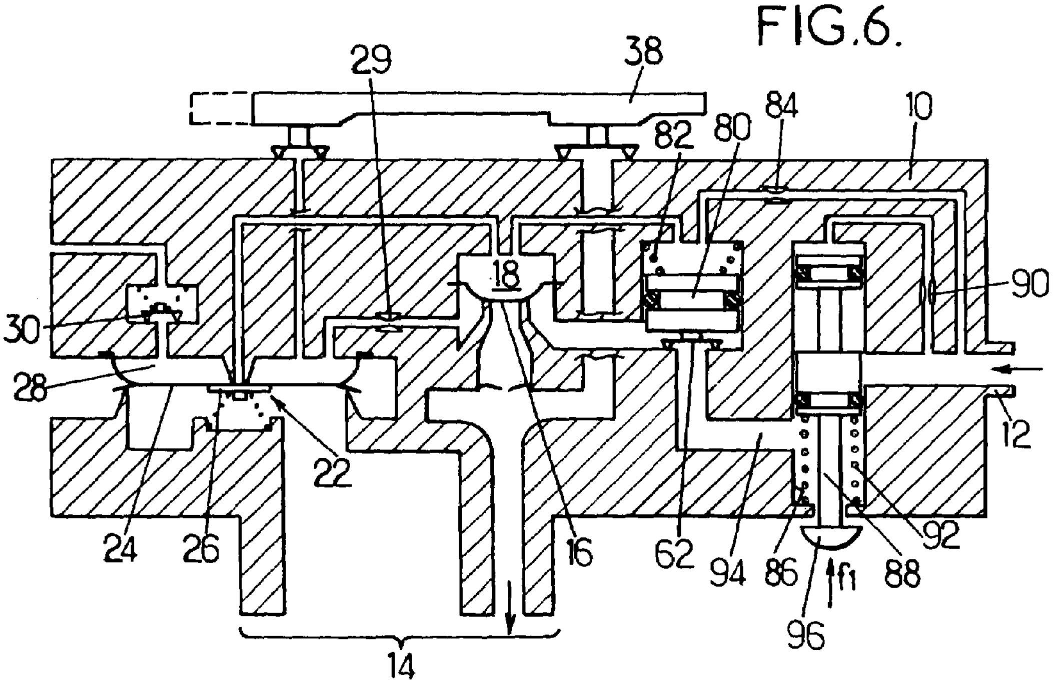

STANDBY REGULATOR FOR BREATHING SYSTEM

BACKGROUND OF THE INVENTION

Breathing protection systems for the crew of aircraft likely to fly at high altitude include a regulator for feeding a breathing mask from a source of pressurized breathing gas (generally oxygen). The regulator can be carried by the mask or it can be mounted on the seat of the crew member.

Usually, such regulators include two selector members made available to the user:

- a button for switching between normal and 100%, thereby enabling the mask to be fed with breathing gas that is diluted with air or else with pure gas; and
- an "emergency" button which, when activated from a rest position, causes the mask to be fed at high pressure.

The user thus has four possible operating states available:

1) normal, for use against insufficient oxygen;
2) 100%, rarely used, except for improving night vision;
3) normal in "emergency" mode, which should be avoided since the high pressure would give rise to a continuous leak through the air inlet; and
4) 100% in "emergency" mode for protecting the wearer against smoke and toxic gas by means of the high pressure which opposes ingress of air and/or depressurization of the environment at high altitude.

The inventors have found that it suffices, in fact, to have only states 1 and 4 available, state 4 being able to replace state 2 without drawback, particularly since state 2 is little used.

SUMMARY OF THE INVENTION

It is an object of the invention to provide type of demand regulator that nevertheless satisfies all requirements.

To this end, the invention provides in particular a demand regulator comprising:

- communication means for putting an admission designed to be connected to a source of pressurized breathing gas into communication with a tube designed to be connected to the inside of a breathing mask;
- means for delivering dilution air to the breathing gas;
- a valve for breathing out from inside the mask to the atmosphere;
- a manual control member having a normal position giving rise to operation without high pressure and with dilution, and an emergency position giving rise to the inside of the mask being fed with pure breathing gas at high pressure; and
- means for preventing operation with pressurized gas feed so long as the mask is in a storage position.

The last disposition is to prevent the mask being stored while operating at high pressure. Under such circumstances, the mask would be fed continuously from the source, and the source would rapidly be depleted.

The means enabling the last function to be performed are advantageously designed so that the mask can be stored (or must necessarily be stored) with the manual control member in the emergency position. This improves safety, since the crew member is supplied with pure breathing gas at high pressure as soon as the mask is put on the face. The same result can be obtained, when the demand regulator is mounted on the mask, by providing its storage box with means that bring the manual control member into the normal position when the mask is stored and that bring it into the emergency position when the mask is extracted.

Other dispositions enable a comparable result to be obtained, e.g. by detecting: that the mask has been taken from its storage box; that the mask has been applied to the face; the mask is forcibly applied to the face; or a harness holding the mask on the face is tensioned, etc. The means used can be mechanical, electrical, or electronic.

The above characteristics and others will appear more clearly on reading the following description of particular embodiments, given as non-limiting examples. The description refers to the accompanying drawings.

BRIEF DESCRIPTION OF THE DRAWINGS

FIG. 1 is a sketch of a demand regulator carried by a breathing mask and constituting a particular embodiment, the figure not being drawn to scale for greater clarity;

FIG. 2, similar to a fraction of FIG. 1, shows a modified embodiment;

FIGS. 3 and 4, likewise similar to fractions of FIG. 1 show other variants;

FIG. 6, likewise similar to FIG. 1, shows yet another embodiment.

DETAILED DESCRIPTION

Figure 5:
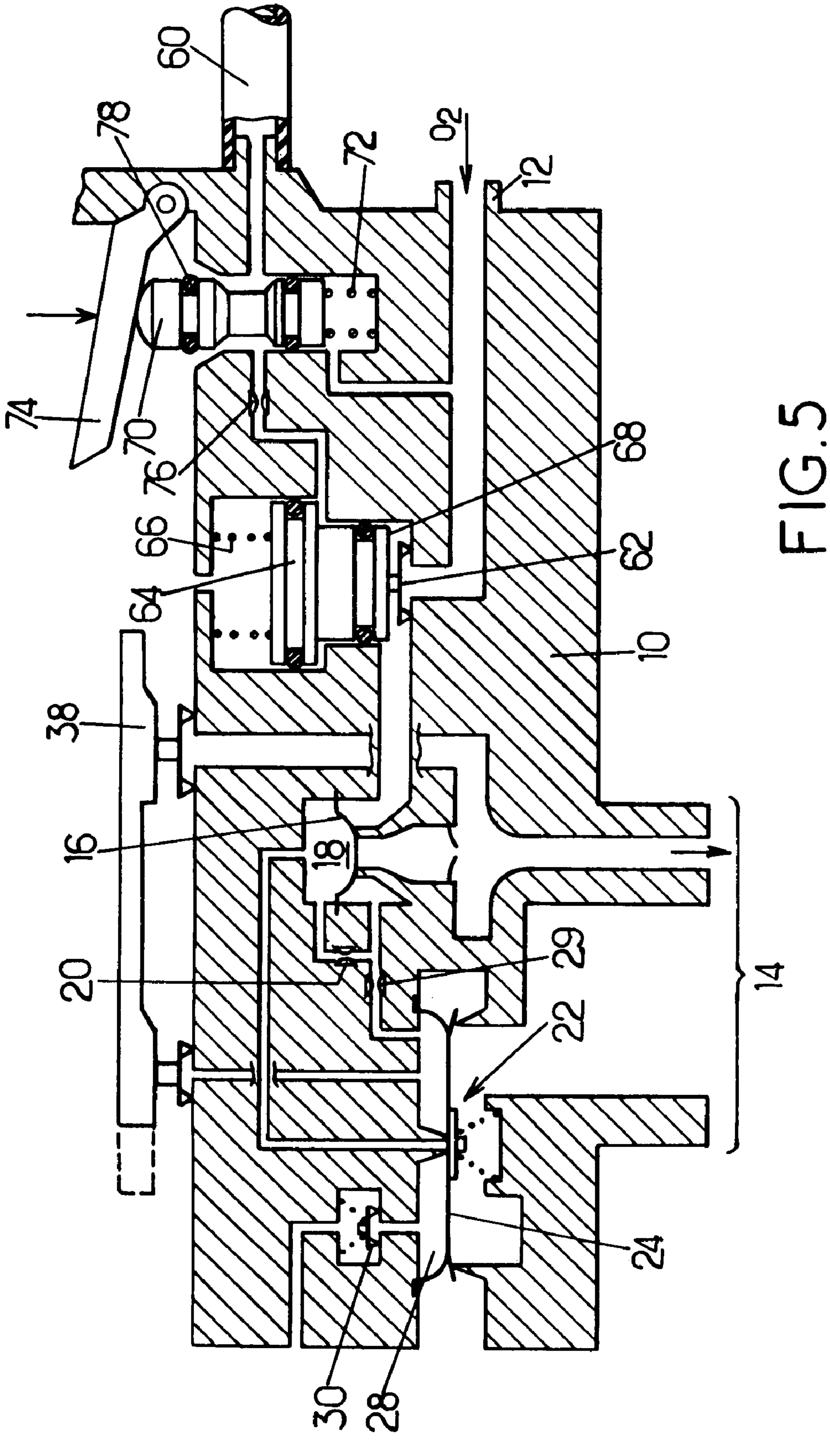
FIG. 5, still similar to FIG. 1, shows an embodiment that can be used when the demand regulator is fitted with an inflatable retention system.

The demand regulator whose general structure is shown in FIG. 1 comprises a housing 10 made up of a plurality of assembled-together pieces, having an admission 12 for connection to a source of pressurized breathing gas, e.g. constituted by a cylinder of oxygen underpressure or a liquid oxygen converter. The housing also has a tube 14 for connection with the inside of a breathing mask (not shown) carrying the regulator.

The housing 10 contains a main valve 16 constituted by a diaphragm co-operating with a fixed seat. A control chamber 18 defined by the rear surface of the main diaphragm and the housing is connected via a constriction 20 to the admission. When it is subjected to admission pressure, the diaphragm 16 is pressed against the seat, closing the passage in said seat, and separating the admission 12 from the tube 14.

The pressure that exists in the chamber 18 is controlled by a pilot valve 22. The pilot valve comprises a diaphragm 24 that is sensitive to pressure. The diaphragm carries a shutter or closure member 26 which co-operates with a fixed seat to put the control chamber 18 into communication with a chamber 28 defined by the diaphragm 24, or to separate the chambers.

The chamber 28 also communicates with the admission via a constriction 29.

The pressure that exists inside the chamber 28 is limited by a valve 30 discharging to atmosphere and which prevents the high pressure in the chamber 28 exceeding a predetermined value.

To enable operation with dilution, an ejector 32 is interposed between the main valve 16 and the tube 14. When open, a passage 34 allows dilution air to arrive downstream from the ejector.

The pilot valve 22 is made in such a manner as to serve also as an exhaust valve. For this purpose, the diaphragm 24 has an annular rim 36 which bears against a seat for exhausting to the atmosphere.

The disposition described above is known and it is used by numerous demand regulators, so its operation need not be described in detail.

To enable the invention to be implemented, the FIG. 1 regulator includes a selector member 38 which is drawn in continuous lines in its "emergency" position and in dashed lines in its "normal" position. This selector member is guided on the housing 10 by means that are not shown. Advantageously, resilient retaining means, such as a ball urged by a spring serves to hold it in whichever position it has been moved manually.

The selector member 38 controls a dilution valve 40 which closes the passage 34 when the member 38 is in its "emergency" position and opens it when the member is in its "normal" position.

The selector member 38 also controls a valve 42 which opens a passage for putting the chamber 28 into communication with the atmosphere when in the "normal" position, and for closing this passage when in the "emergency" position.

It is explained below that the elimination of any communication between the chamber 28 and the atmosphere causes the mask to be fed at a high pressure which is set by the rating of the valve 30. Consequently, except when the supply of pressurized breathing gas to the regulator is prevented by other means, the chamber 28 must remain connected to the atmosphere so long as the mask is not in use.

For this purpose, the regulator shown in FIG. 1 has a valve 44 connecting the chamber 28 to the atmosphere, which valve is urged by a spring 46 towards an open position. The valve 44 is provided with a push rod 48 which projects from the housing 10 at rest. This push rod is designed to be pushed in and to close the valve 44 when the mask fitted with the regulator is placed on the face. The push rod can be designed to press against the face. It can also be placed in such a manner as to be pushed in when a harness that holds the mask against the face is under tension. The spring 48 can be rated either so that mere contact between the push rod 48 and the face suffices to close the valve, or else so that the valve 44 closes only when sufficient application force is exerted.

When the regulator is in its "normal" state it operates in conventional manner and that is why there is no need to describe such operation herein.

However, when the selection member 38 is in its "emergency" position, and the valve 44 is closed, then the regulator operates as follows.

Because the chamber 28 is separated from the atmosphere, the admission pressure tends to become established therein via the constriction 29. However, the pressure in the chamber 28 is limited by the atmospheric bleed valve 30 opening when the pressure reached in the chamber 28 is sufficient to open the pilot valve 22. The pressure in the control chamber 18 drops to a value fixed by the rating of the valve 30. The main valve 16 subjected to the difference in pressure between the admission and the pressure in the chamber 18 opens and feeds the tube 14 with pure breathing gas. The main valve 16 opens only when the pilot valve 22 closes under the effect of the increasing pressure inside the mask.

When the user breathes out, the annular rim 36 lifts off its seat and exhausts to the atmosphere.

The regulator does not discharge to atmosphere even when the selector member 30 is in its "emergency" position so long as the valve 44 remains open, and thus so long as the mask is not in place.

In the modified embodiment shown in FIG. 2, the box 52 for receiving the mask is designed to bring and/or retain the selection member 30 into the "normal" position so long as the mask is in storage, and to cause it to pass into its "emergency" position when the mask is taken out.

For this purpose, the box has a resilient catch 54 and the selector member 38 has a stud 56. When the mask fitted with the regulator is pushed into the box in the direction of arrow f, the catch begins by pushing the member 38 to the left until it has been brought into its "normal" position, after which it snaps into position beyond the stud. When the mask is pulled out, the resilient catch 54 returns the member 38 to the "emergency" position before retracting.

The FIG. 3 embodiment can be considered as having a push rod whose operation is the opposite to that of the rod of FIG. 1. In FIG. 3, where the members corresponding to those of FIG. 1 are given the same reference numerals, the valve 44*a* is urged by a spring 46*a* towards its open position. The push rod 48*a* is arranged to be pushed in and to open the valve 44*a* when the mask fitted with its regulator is placed in the box 52*a*.

The embodiment shown in FIG. 4 is particularly suitable for use when the regulator is mounted on the mask and is suitable for storage in a box. High pressure operation with the selector member 38 in the "emergency" position occurs in response to the first breathing causing the pressure in the tube to drop below ambient pressure. The constriction 29 of FIG. 1 is omitted.

When the admission 12 is fed and the selection member 38 is in the "emergency" position, while ambient pressure is too low to open the valve 30, the main valve 16 remains closed. The chamber 28 is separated from the admission by the pilot valve 26 which is held closed by the spring 50. Admission pressure then exists in the chamber 18.

On first breathing in by the wearer of the mask, an under pressure is established in the tube 14. The admission pressure then tends to become established in the chamber 28 and holds the pilot valve continuously open. Nevertheless, the pressure is limited by the continuously open pilot valve. Nevertheless, the pressure is limited by the atmospheric bleed valve 30 to a value that is low enough for the main valve to remain open and high enough for the main valve to remain likewise open.

When the regulator is in the "emergency" position, surrounding depressurization causes the valve 30 to open and decreases the pressure in the chamber 18 to a level such that the main valve delivers gas continuously. To avoid this situation when the mask is not being worn, the mask is generally stored in a box:

which automatically brings it to the "normal" position (FIG. 2); or which prevents it from being stored in the "emergency" position, e.g. by holding the mask at the entrance to the box when the selection member is in its "emergency" position.

The embodiment of FIG. 5 is designed to be carried by a mask. It differs from that of FIG. 1 in that its operation, even in the "emergency" position, depends on an inflation of a mask pneumatic harness, e.g. of the kind described in application FR 98/05949 or patent U.S. Pat. No. 5,690,102.

The regulator proper has the same structure as that of FIG. 1, except that it does not have the valve 44 which closes when the mask is pressed against the face. However, the housing 10 also contains a mechanism for inflating and adjusting the pressure in a harness 60 for retaining the mask.

The admission 12 of pressurized breathing gas is connected to the annular chamber situated beneath the diaphragm of the main valve only in response to a valve 62 opening under the control of a differential piston 64. A spring 66 urges the piston 64 towards a position in which the valve 62 is pressed against its seat. Under such circumstances, the inability of the regulator to operate is due to its supply being cut off.

The larger surface of the piston 64 is subjected to atmospheric pressure and tends to close the valve 62. The smaller surface of the piston is subject to the pressure which exists downstream from the valve 62. The annular surface 68 constituted by the staged configuration of the piston is subjected to a pressure that is controlled by a cock for inflating and deflating the harness 60.

The cock can be of various structures. In FIG. 5, a passage 72 is provided in the housing. The passage has a plunger 70 received therein which constitutes a double-acting shutter member. One end of the passage is connected to the inlet for pressurized breathing gas. Its other end opens to atmosphere. A first O-ring carried by the plunger 70 bears against a cylindrical portion of the passage and separates the gas admission from the harness while the plunger 70 is held by the admission pressure so as to bear against the control lug 74 while the lug is in its rest position. When the lug 74 is pushed in manually, it pushes the plunger to a position in which it puts the gas admission into communication with the harness. Simultaneously, the displacement of the plunger brings a second O-ring 78 into contact with a frustoconical portion of the passage and separates the harness from the atmosphere.

A constricted passage 76 enables the pressure which exists inside the harness to be established also against the annular surface 68.

When not in use, a mask fitted with the regulator shown in FIG. 5 will normally be stored in a box that leaves the regulator projecting therefrom so that it can be seized. The box is provided with doors that open when the user pulls on the mask. In general, the box is provided with a cock that is opened by the doors being opened. Nevertheless, such a cock is not essential.

Even if the member ~38 is in its "emergency" position, the regulator does not deliver oxygen. The main valve is not fed because the valve 62 is closed by the spring 66.

When the user of the mask pushes down the plunger 70 in order to inflate the harness, admission pressure becomes established progressively against the annular surface 68. The piston 64 rises and opens the valve 62. From this point on, operation is the same as that of the FIG. 1 embodiment when its valve 44 is closed.

When the user releases the plunger 70 in order to deflate the harness, the valve 62 does not close. The admission pressure then acting on the bottom face of the piston 64 holds it in the high position.

Even if the valve 62 is open, the regulator no longer delivers when the mask is not pressed against the face and the member 38 is in the "normal" position.

The embodiment shown in FIG. 6 has a regulator proper that differs from that shown in FIG. 5 only by the absence of the constricted communication 20.

The regulator has underpressure controlled means which isolate the regulator proper from the admission, as in FIG. 5, until an underpressure appears relative to ambient pressure inside the tube 14, i.e. the pressure reduction caused by first inspiration.

This first intake of breath causes the pressure in the tube to decrease and opens the pilot valve 22. Admission pressure then tends to become established inside the chamber 28 and to hold the pilot valve 22 open. This pressure becomes established from the admission 12 via a constriction 84 and the connections via the command chamber 18.

Additional means are provided in the FIG. 6 configuration to slow down the opening of the main valve 16. These means comprise a piston 80 sliding in a bore of the housing and urged by a spring 82 towards a position in which it closes a stop valve 62 that prevents breathing gas from reaching the main valve. The timing elements further include a plunger 88 which slides in a bore 86 and has a structure comparable to that of the plunger 70 in FIG. 5. One of the end faces of the plunger is subjected to the pressure that exists in a compartment connected to the admission via a constriction 90. The other end face of the plunger is subjected to atmospheric pressure when the plunger is in the rest position shown in FIG. 6. This pressure is communicated to the upstream side of the valve 62 by a passage 94.

So long as the breathing gas pressure does not exist in the admission 12, the plunger 88 remains in the position shown in FIG. 6. Once said pressure is established, e.g. because a cock has been opened under the control of the doors of the storage box, then the pressure which acts on the end face of the piston increases progressively at a rate which is fixed by the constriction 90. The plunger 88 is pushed back progressively against spring 92 towards a position in which it separates the passage 94 from the atmosphere and puts it into communication with the admission. The valve 62 can then feed the main valve.

Once the plunger is in the position communicating the admission with the main valve, the plunger remains in that position. A push rod 96 can be provided to return to its rest position by action in the direction of arrow fl.

All of the embodiments described above operate in purely pneumatic manner. The invention can also be used in a regulator making use of sensors, solenoid valves, and/or piezoelectric actuators, e.g. of the kind described in document U.S. Pat. No. 4,336,590 (French patent No. 79/11072) to which reference can be made.

More generally, the means for preventing operation with the mask being fed with pressurized gas so long as the mask is in a storage position can have a very wide variety of structures. If the regulator is carried by a mask, the means can be controlled by inflating the harness, by deflating the harness after inflation, by measuring forces on the harness, by measuring the force with which the mask is pressed against the face, by detecting the presence of the face. The means can be responsive to a first intake of breath giving rise to a vacuum in the mask after it has been put on the face. The means can prevent a mask fitted with a regulator from being stored in a box while it is in the "emergency" position. When the regulator is separate from the mask, a communication can be provided between the mask and the regulator to transmit reliable information to the regulator. A disposition of the kind shown in FIG. 6 can be used.

In any event, operation can be prevented by cutting off the feed upstream from the regulator, by cutting off the flow passing through the regulator, or by cutting off the high pressure, and the various solutions can be used in combination.

What is claimed is:

1. A demand regulator comprising:

a tube for connection with the inside of a breathing mask;

an admission of pressurized breathing gas communicating with said tube;

a main valve disposed between the admission and the tube, said main valve defining a control chamber separated from admission by a diaphragm subjected to pressure, said control chamber being connected to the admission via a constriction;

an ejector interposed between the main valve and the tube;

a passage adapted for allowing dilution air to arrive downstream from the ejector;

a pilot valve defining a chamber separated from said tube by a diaphragm responsive to breath-in suction, said chamber being in communication with the admission;

a shutter carried by said pilot valve diaphragm, suitable for putting into communication said control chamber with said pilot valve chamber or for separating said chambers;

a passage for putting said pilot valve chamber into communication with the atmosphere;

a valve discharging to atmosphere for limiting pressure in the pilot valve chamber;

a selector member carrying a first valve and a second valve, said selector member being displaceable between an emergency position wherein said first valve closes said dilution air passage and said second valve closes said passage for putting said pilot valve chamber into communication with the atmosphere, thereby feeding said tube with pure breathing gas at an over pressure, and a normal position wherein said first valve opens said dilution air passage and said second valve opens said passage for putting said pilot valve chamber into communication with the atmosphere, thereby feeding said tube with diluted gas without over pressure; and a member which cooperates with a storage box, when the demand regulator with the mask is in a mask storage box, to cause said pilot valve chamber to be in communication with the atmosphere.

2. A demand regulator according to claim 1, wherein the member is a control valve having (a) an open position whereby said valve opens a passage for putting said pilot valve chamber into communication with the atmosphere when said mask is stored in the storage box, and (b) a closed position wherein said valve closes said passage when the mask is placed on a face of a user.

3. A demand regulator according to claim 1, wherein said control valve has a push rod which projects from a housing of the regulator, said push rod being adapted for being pressed against the face of the user.

4. A demand regulator according to claim 1, wherein the member is said selector member which is adapted for cooperating with a catch of the mask storing box, which catch places the selector member in normal position when the mask is stored in the box, and in emergency position when the mask is taken out from the box.

5. A demand regulator according to claim 4, wherein the selector member has a stud adapted for cooperating with a resilient catch of the mask storing box, whereby, when the mask is pushed into the box the catch brings the selector member in the normal position and snaps into position beyond the stud, whereas when the mask is taken out from the box the resilient catch brings the selector member back to emergency position before retracting.

* * * * *